US012029783B2

(12) United States Patent
Bartsich (10) Patent No.: US 12,029,783 B2
(45) Date of Patent: *Jul. 9, 2024

(54) MAMMARY TUMOR VIRUS VACCINE

(71) Applicant: VIRAGO VAX INC., New York, NY (US)

(72) Inventor: Sophie Bartsich, New York, NY (US)

(73) Assignee: VIRAGO VAX INC., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/460,295

(22) Filed: Jul. 2, 2019

(65) Prior Publication Data

US 2019/0343938 A1 Nov. 14, 2019

(51) Int. Cl.
| A61K 39/00 | (2006.01) |
| A61K 39/15 | (2006.01) |
| A61K 39/295 | (2006.01) |
| A61P 31/14 | (2006.01) |

(52) U.S. Cl.
CPC .......... *A61K 39/0011* (2013.01); *A61K 39/15* (2013.01); *A61K 39/295* (2013.01); *A61P 31/14* (2018.01); *A61K 2039/585* (2013.01)

(58) Field of Classification Search
None
See application file for complete search history.

(56) References Cited

U.S. PATENT DOCUMENTS

| 6,258,932 B1 * | 7/2001 | Vahlne ..................... A61P 31/18 530/331 |
| 6,670,466 B1 * | 12/2003 | Garry ................... C07K 14/005 536/23.72 |
| 9,383,367 B1 | 7/2016 | Liu et al. |
| 2007/0281911 A1 | 12/2007 | Cihlar et al. |
| 2009/0269364 A1 | 10/2009 | Zielinski et al. |
| 2012/0135950 A1 | 5/2012 | Kaplan et al. |
| 2014/0271687 A1 | 9/2014 | Kovesdi et al. |
| 2015/0174237 A1 | 6/2015 | Mond et al. |
| 2019/0343938 A1 | 11/2019 | Bartsich |

FOREIGN PATENT DOCUMENTS

| WO | 9951268 | 10/1999 |
| WO | 1999051267 A1 | 10/1999 |
| WO | WO1999051268 | * 10/1999 |
| WO | 2017147078 A1 | 8/2017 |

OTHER PUBLICATIONS

Iaria et al. (Vaccine vol. 32, pp. 1072-1078 (Year: 2014).*
Laria et al. (Vaccine vol. 32, pp. 1072-1078 (Year: 2014).*
Hizi et al. (J of Virology vol. 63, pp. 2543-2549, 1989). (Year: 1989).*
Macias-Perez et a., The Journal of Biological Chemistry vol. 283, No. 18, pp. 12538-12545, 2008 (Year: 2008).*
Begg et al., Vaccine, vol. 13, No. 16, pp. 1547-1550 (Year: 1995).*
Braitbard et al., Oncotarget, vol. 7, No. 16, pp. 21168-21180 (Year: 2016).*
Bryson et al., Vaccine vol. 35, pp. 5842-5849 (Year: 2017).*
Denner et al. (Virus Research vol. 208, pp. 39-43 (Year: 2008).*
Barouch—Nature vol. 455 Oct. 2, 2008 doi:10.1038/nature07352 (Year: 2008).*
Levine P. Increasing evidence for a human breast carcinoma virus with geographic differences. Cancer, 2004. 101: 721-726.
Levine P. Increased detection of breast cancer virus sequences in inflammatory breast cancer. Adv Tumor Virol. 2009. 1: 3-7.
Links J. The Growth Accelerating Effect of Bittner Virus in Monolayers of Baby Mouse Kidney Cells. J. Gen Virol, 1969. 5:547-550.
Litvinov S. Expression of proteins immunologically related to murine mammary tumor virus (MMTV) core proteins in cells of breast cancer continuous cell lines MCF7, T47D, MDA-MB231 and cells from human milk. Acta Virol. 1989. 33: 137-142.
Liu B. Identification of a proviral structure in human breast cancer. Cancer Res, 2001. 61: 1754-1759.
Lloyd R. Murine mammary tumor virus related antigen in human male mammary carcinoma. Cancer, 1983. 51: 654-661.
Lower R. The pathogenic potential of endogenous retroviruses: facts and fantasies. Trends in Microbiology, 1999. 7: 9, 350-356.
Luo T. Study of mouse mammary tumor virus-like gene sequences expressing breast tumors of Chinese women. Sichuan Da Xue Xue Bao Yi Xue Ban, 2006. 37: 844-846.
Lynch H. Is cancer communicable? Med Hypotheses, 1984. 14: 181-198.
MacMahon B. Etiology of human breast cancer: a review. J Natl Cancer Inst. 1973. 50:21-42.
Mager D. HERV-H endogenous retroviruses: presence in the new world branch but amplification in the old world primate lineage. Virology, 1995. 213: 395-404.
Mager D. Novel Mouse Type D Endogenous Proviruses and Elements Share Long Terminal Repeat and Internal Sequences. J Virology, 2000. 74: 16, 7221-7229.
Mant C. A human murine mammary tumor virus-like agents are genetically distinct from endogenous retroviruses and not detectable in breast cancer cell lines of biopsies. Virology, 2004. 318: 393-403.
Marchetti A. Host Genetic Background Effect o the Frequency of Mouse Mammary Tumor Virus—Induced Rearrangements of the int-1 and int-2 Loci in Mouse Mammary Tumors. J Virology, 1991. 65: 8, 4550-4554.

(Continued)

*Primary Examiner* — Shanon A. Foley
*Assistant Examiner* — Myron G Hill
(74) *Attorney, Agent, or Firm* — Grogan, Tuccillo & Vanderleeden, LLP (57) ABSTRACT

Disclosed is a vaccine containing an MTV transition protein. A further version of the invention is a vaccine comprising MTV polypeptides coupled to a carrier protein. MTV may be treated by providing an MTV vaccine with an MTV transition protein; and, administering said vaccine.

15 Claims, 3 Drawing Sheets

Specification includes a Sequence Listing.

(56) References Cited

OTHER PUBLICATIONS

Marrack P. A maternally inherited superantigen encoded by a mammary tumour virus. Nature, 1991. 349:524-525.

Melana S. Search for mouse mammary tumor virus-like env sequences in cancer and normal breast from the same individuals. Clin Cancer Res, 2001. 7: 283-284.

Melana S. Characterization of viral particles isolated from primary cultures of human breast cancer cells. Cancer Res, 2007. 67:8960-8965.

Moore D. Search for a human breast cancer virus. Nature, 1971. 229: 611-615.

Mueller-Lantzsch N. Human Endogenous Retroviral Element K10 (KERV-K10) Encodes a Full-Length Gag Homologous 73-kDa Protein and a Functional Protease. AIDS Research and Human Retroviruses, 1993. 9: 4, 343-350.

Nusse R. The int genes in mammary tumorigenesis and in normal development. TIG, 1988. 4: 10, 291-295.

Ono M. Stimulation of Expression of the Human Endogenous Retrovirus Genome by Female Steroid Hormones in Human Breast Cancer Cell Line T47D. Journal of Virology, 1987. 61:2059-2062.

Paces J. HERV: database of human endogenous retroviruses. Nucleic Acids Research, 2002. 30:1, 205-206.

Palmarini M. The Exogenous Form of Jaagsiekte Retrovirus is Specifically Associated with a Contagious Lung Cancer of Sheep. J of Virology, 1996. 70: 3, 1618-1623.

Peters G. Tumorigenesis by Mouse Mammary Tumor Virus: Evidence for a Common Region for Provirus Integration in Mammary Tumors. Cell, 1983. 33:36-377.

Pogo B. Detection of mammary tumor virus env gene-like sequences in human breast cancer. Cancer Res, 1995. 55:5173-5179.

Pogo B. Sequences homologous to the MMTV env gene in human breast carcinoma correlate with overexpression of laminin receptor. Clin Cancer Res. 1999. 5: 2108-2111.

Prak E. Mobile Elements and the Human Genome. Nature Reviews Genetics, 2000. 1: 134-144.

Reus K. HERV-K (OLD): Ancestor Sequences of the Human Endogenous Retrovirus Family HERV-K (HNL-2). J Virology, 2001. 75: 19, 8917-8926.

Reuss F. cDNA Sequence and Genomic Characterization of Intracisternal A-Particle-Related Retroviral Elements Containing an Envelope Gene. J Virology, 1991. 65: 11, 5702-5709.

Rous P. A sarcoma of the fowl transmissible by an agent separable from the tumor cells. J Exp Med, 1911. 13: 397.

Russ J. Identical cancers in husband and wife. Surg Gynecol Obstet, 1980. 150: 664-666.

Salmons B. Production of mouse mammary tumor virus upon transfection of a recombinant proviral DNA into cultured cells. Virology, 1985. 144: 101-114.

Shackleford G. Mouse mammary tumor virus infection accelerates mammary carcinogenesis in Wnt-1 transgenic mice by insertional activation of int-1/Fgf-3 and hst/ Fgf-4. Proc Natl Acad Sci USA, 1993. 90:740-744.

Smit A. Interspersed repeats and other mementos of transposable elements in mammalian genomes. Current Opinion in Genetics & Development, 1999. 9: 657-663.

Stewart A. Identification of Human Homologues of the Mouse Mammary Tumor Virus Receptor. Archives of Virology, 2002. 147:577-581.

Stewart S. Burkitt's tumour: tissue culture, cytogenetic and virus studies. J Nat Cancer Inst, 1964. 34: 319.

Stewart T. Breast Cancer Incidence Highest in the Range of One Species of House Mouse, *Mus domesticus*. British Journal of Cancer, 2000. 82:446-451.

Sumidaie A. Particles with Properties of Retroviruses in Monocytes from Patients with Breast Cancer. The Lancet, 1988. 5-9.

Szabo S. of Mice, Cats and Men: Is human breast cancer a zoonosis? Microsc Res Tech, 2005. 68:197-208.

Tchenio T. Defective Retroviruses Can Disperse in the Human Genome by Intracellular Transposition. Journal of Virology, 1991. 65:2113-2118 Time, Cancer Virus, Mar. 18, 1946.

Tonjes R. Characterization of Human Endogenous Retrovirus Type K Virus-like Particles Generated from Recombinant Baculoviruses. Virology, 1997. 233: 280-291.

Tristem M. Identification and Characterization of Novel Human Endogenous Retrovirus Families by Pylogenetic Screening of the Human Genome Mapping Project Database. J Virology, 2000. 74:8, 3715-3730.

Tsubura A. Intervention of T-cells in transportation of mouse mammary tumor virus to mammary gland cells in vivo. Canc. Res, 1988 48:6555-59.

Turner G. Insertional polymorphisms of full-length endogenous retroviruses in human. Current Biology, 2001. 11:1531-1535.

Wang Y. Detection of mammary tumor virus env gene-like sequences in human breast cancer. Cancer Res, 1995. 55:5173-5179.

Wang Y. Detection of MMTVlike LTR and LTR-env gene sequences in human breast cancer. Int J Oncology, 2001. 18:1041-1044.

Wang Y. Presence of MMTV-like env gene sequences in gestational breast cancer. Med Oncol, 2003. 20: 233-236.

Wang Y. A mouse mammary tumor virus-like long terminal repeat superantigen in human breast cancer. Cancer Res, 2004. 64: 4105-4111.

Westley B. The human genome contains multiple sequences of varying homology to mouse mammary tumour virus DNA. Gene, 1984. 28:221-227.

Witkin A. Antigens and antibodies cross-reactive to the murine mammary tumor virus in human breast cyst fluids. J Clin Invest, 1981. 67:216-222.

Witt A. The mouse mammary tumor virus-like sequence is not detectable in breast cancer tissue of Austrian patients. Oncol Rep, 2003. 10: 1025-1029.

Wright D. Burkitt's tumor and childhood lymphosarcoma. Clin Ped. 1967. 6: 116.

Xu L. Does a betaretrovirus infection trigger primary biliary cirrhosis? Proc Natl Acad Sci, 2003. 100: 8454-8459.

Yang M. Presence of a mouse mammary tumor virus MMTV-related antigen in human breast carcinoma cells and its absence from normal epithelial cells. J Natl Cancer Inst, 1978. 61:1205-1207.

Zammarchi F. MMTV-like sequences in human breast cancer: a fluorescent PCR/laser microdissection approach. Journal of Pathology, 2006. 209:436-444.

Zapata-Benavides P. Mouse mammary tumor virus-like gene sequences in breast cancer samples of Mexican women. Intervirology, 2007. 50:402-407.

Alibek K, Kakpenova A, Mussabekova A, Sypabekova M, Karatayeva N. Role of viruses in the development of breast cancer. Infect Agent Cancer 2013;8:32.

Mirzaei H, Faghihloo E. Viruses as key modulators of the TGF-β pathway; a double-edged sword involved in cancer. Rev Med Virol 2018;28(2).

Reza MA, Reza MH, Mahdiyeh L, Mehdi F, Hamid ZN. Evaluation Frequency of Merkel Cell Polyoma, Epstein-Barr and Mouse Mammary Tumor Viruses in Patients with Breast Cancer in Kerman, Southeast of Iran. Asian Pac J Cancer Prev 2015;16(16):7351-7.

Carolis S, Pellegrini A, Santini D, et al. Liquid biopsy in the diagnosis of HPV DNA in breast lesions. Future Microbiol 2018;13:187-194.

Franklin GC, Chretien S, Hanson IM, Rochefort H, May FE, Westley BR. Expression of human sequences related to those of mouse mammary tumor virus. J Virol 1988;62(4):1203-10.

Etkind PR, Alexandre FR, Wiernik PH. Mouse mammary tumor virus (MMTV)-like DNA sequences in the breast tumors of father, mother, and daughter. Infect Agent Cancer 2008;3(2).

Szakacs JG, Moscinski LC. Sequence homology of deoxyribonucleic acid to mouse mammary tumor virus genome in human breast tumors. Ann Clin Lab Sci 1991;21(6):402-12.

Naushad W, Bin Rahat T, Gomez MK, Ashiq MT, Younas M, Sadia H. Detection and identification of mouse mammary tumor virus-like DNA sequences in blood and breast tissues of breast cancer Tumour Biol 2014;35(8):8077-86.

(56) References Cited

OTHER PUBLICATIONS

Wang F, Hou J, Shen Q, et al. Mouse mammary tumor virus-like virus infection and the risk of human breast cancer: a meta-analysis. Am J Transl Res 2014;6(3):248-66.
May FE, Westley BR, Rochefort H, Buetti E, Diggelmann H. Mouse mammary tumour virus related sequences are present in human DNA. Nucleic Acids Res 1983;11(12):4127-39.
Kincaid RP, Panicker NG, Lozano MM, Sullivan CS, Dudley JP, Mustafa F. MMTV does not encode viral microRNAs out alters the levels of cancer-associated host microRNAs. Virology 2018;513:180-187.
Day NK, Witkin SS, Sarkar NH, et al. Geographic and family studies of immunological responses to antigens of the murine mammary tumor virus in sera of patients with breast cancer. Trans Assoc Am Physicians 1980;93:123-9.
Lawson JS, Glenn WK, Whitaker NJ. Human Papilloma Viruses and Breast Cancer—Assessment of Causality. Front Oncol 2016;6:207.
Xue XY, Majerciak V, Uberoi A, et al. The full transcription map of mouse papillomavirus type 1 (MmuPV1) in mouse wart tissues. PLoS Pathog 2017;13(11):e1006715.
Froissart R, Wilke CO, Montville R, Remold SK, Chao L, Turner PE. Co-infection weakens selection against epistatic mutations in RNA viruses. Genetics. 2004;168(1):9-19.
Crépin M, Lidereau R, Chermann JC, et al. Sequences related to mouse mammary tumor virus genome in tumor cells and lymphocytes from patients with breast cancer. Biochem Biophys Res Commun 1984;118(1):324-31.
Lopez DM, Parks WP, Silverman MA, Distasio JA. Lymphoproliferative responses to mouse mammary tumor virus in lymphocyte subsets of breast cancer patients. J Natl Cancer Inst 1981;67(2):353-8.
Johal H, Ford C, Glenn W, Heads J, Lawson J, Rawlinson W. Mouse mammary tumor like virus sequences in breast milk from healthy lactating women. Breast Cancer Res Treat 2011;129(1):149-55.
Finn OJ, Rammensee HG. Is it Possible to Develop Cancer Vaccines to Neoantigens, What Are the Major Challenges, and How Can These Be Overcome? Neoantigens: Nothing New in Spite of the Name. Cold Spring Harb Perspect Biol 2017;pii: a028829.
Lawson JS, Glenn WK, Salmons B, Ye Y, Heng B, Moody P, Johal H, Rawlinson WD, Delprado W, Lutze-Mann L, Whitaker NJ. Mouse mammary tumor virus-like sequences in human breast cancer. Cancer Res 2010;70(9):3576-85.
Crépin M, Lidereau R, Chermann JC, Pouillart P, Magdamenat H, Montagnier L. Sequences related to mouse mammary tumor virus genome in tumor cells and lymphocytesfrom patients with breast cancer. Biochem Biophys Res Commun 1984;118(1):324-31.
Deligdisch L, Marin T, Lee AT, et al. Human mammary tumor virus (HMTV) in endometrial carcinoma. Int J Gynecol Cancer 2013;23(8):1423-8.
Svec J, Hlavay E, Matoska J, Thurzo V. Hormone-responsive genes of the mouse mammary tumor virus. Czech Med 1979;2(4):198-212.
Pogo BG, Holland JF, Levine PH. Human mammary tumor virus in inflammatory breast cancer. Cancer 2010;116(11 Suppl):2741-4.
Perzova R, Abbott L, Benz P, et al. Is MMTV associated with human breast cancer? Maybe, but probably not. Virol J 2017;14(1):196.
Duesberg PH, Blair PB. Isolation of the nucleic acid of mouse mammary tumor virus (MTV). Proc Natl Acad Sci U S A 1966;55(6):1490-7.
Vinner L, Mourier T, Friis-Nielsen J, et al. Investigation of Human Cancers for Retrovirus by Low-Stringency Target Enrichment and High-Throughput Sequencing. Sci Rep 2015;5:13201.
Bozorgi A, Khazaei M, Khazaei MR. New Findings on Breast Cancer Stem Cells: A Review. J Breast Cancer 2015;18(4):303-12.
Al Moustafa AE, Al-Antary N, Aboulkassim T, Akil N, Batist G, Yasmeen A. Co-prevalence of Epstein-Barr virus and high-risk human papillomaviruses in Syrian women with breast cancer. Hum Vaccin Immunother 2016;12(7):1936-9.

Salmons B, Lawson JS, Günzburg WH. Recent developments linking retroviruses to human breast cancer: infectious agent, enemy within or both? J Gen Virol 2014;95(Pt 12):2589-93.
Astori M, Karapetian O. Immunization with a mouse mammary tumour virus envelope protein epitope protects against tumour formation without inhibition of the virus infection. J Gen Virol 1997;78(Pt 8):1935-9.
Atique S, Hsieh Chen, Hsiao RT, et al. Viral warts (Human Papilloma Virus) as a potential risk for breast cancer among young females. Comput Methods Programs Biomed 2017;144:203-207.
San TH, Fujisawa M, Fushimi S, et al. Low prevalence of human mammary tumor virus (HMTV) in breast cancer patients from Myanmar. Infect Agent Cancer 2017;12:20.
Bae JM, Kim EH. Human papillomavirus infection and risk of breast cancer: a meta-analysis of case-control studies. Infect Agent Cancer 2016;11:14.
Ballard AJ. Epstein-Barr virus infection is equally distributed across the invasive ductal and invasive lobular forms of breast cancer. Pathol Res Pract 2015;211(12):1003-5.
Baltzell KA, Shen HM, Krishnamurthy S, Sison JD, Nuovo GJ, Buehring GC. Bovine leukemia virus linked to breast cancer but not coinfection with human papillomavirus: case-control study of women in Texas. Cancer 2018; 124 (7):1342-1349.
Bindra A, Muradrasoli S, Kisekka R, Nordgren H, Warnberg F, Blomberg J. Search for DNA of exogenous mouse mammary tumor virus-related virus in human breast cancer samples. J Gen Virol 2007;88(Pt 6):1806-9.
Stewart TH, Sage RD, Stewart AF, Cameron DW. Breast cancer incidence highest in the range of one species of house mouse, *Mus domesticus*. Br J Cancer 2000;82(2):446-51.
Szabo S, Haislip AM, Traina-Dorge V, et al. Human, rhesus macaque, and feline sequences highly similar to mouse mammary tumor virus sequences. Microsc Res Tech 2005;68(3-4):209-21.
Buehring GC, Shen H, Schwartz DA, Lawson JS. Bovine leukemia virus linked to breast cancer in Australian women and identified before breast cancer development. Plos One 2017;12(6):e0179367.
Callahan R, Mudunur U, Bargo S, et al. Genes affected by mouse mammary tumor virus (MMTV) proviral insertions in mouse mammary tumors are deregulated or mutated in primary human mammary tumors. Oncotarget 2012;3(11):1320-34.
Cedro-tanda A, Córdova-Solis A, Juárez-Cedillo T, et al. Prevalence of HMTV in breast carcinomas and unaffected tissue from Mexican women. BMC Cancer 2014;14:942.
Chouchane L, Boussen H, Sastry KS. Breast cancer in Arab populations: molecular characteristics and disease management implications. Lancet Oncol 2013;14(10):e417-24.
Coghill AE, Engels EA, Schymura MJ, et al. Risk of breast, prostate, and colorectal cancer diagnoses among HIV-infected individuals in the United States. J Natl Cancer Inst 20181;110(9):959-966.
Corbex M, Bouzbid S, Traverse-Glehen A, et al. Prevalence of papillomaviruses, polyomaviruses, and herpesviruses in triple-negative and inflammatory breast tumors from algeria compared with other types of breast cancer tumors. Plos One 2014;9(12):e114559.
De Vries RD, de Swart RL. Measles immune suppression: functional impairment or numbers game? PLoS Pathog 2014;10(12):e1004482.
Dion AS, Girardi AJ, Williams CC, Pomenti AA. Serologic responses to murine mammary tumor virus (MuMTV) in MuMTV-exposed laboratory personnel. J Natl Cancer Inst 1986;76(4):611-9.
Dudley JP, Golovkina TV, Ross SR. Lessons learned from mouse mammary tumor virus in animal models. ILAR J 2016;57(1):12-23.
Tomana M, Kajdos AH, Niedermeier W, Durkin WJ, Mestecky J. Antibodies to mouse mammary tumor virus-related antigen in sera of patients with breast carcinoma. Cancer 1981;47(11):2696-703.
Faschinger A, Rouault F, Sollner J, Lukas A, Salmons B, Günzburg WH, Indik S. Mouse mammary tumor virus integration site selection in human and mouse genomes. J Virol 2008;82(3):1360-7.
Ford CE, Faedo M, Rawlinson WD. Mouse mammary tumor virus-like RNA transcripts and DNA are found in affected cells of human breast cancer. Clin Cancer Res 2004; 10(21):7284-9.

(56) References Cited

OTHER PUBLICATIONS

Ford CE, Tran D, Deng Y, Ta VT, Rawlinson WD, Lawson JS. Mouse mammary tumor virus-like gene sequences in breast tumors of Australian and Vietnamese women. Clin Cancer Res 2003;9(3):1118-20.

Glenn WK, Heng B, Delprado W, Lacopetta B, Whitaker NJ, Lawson JS. Epstein-Barr virus, human papillomavirus and mouse mammary tumour virus as multiple viruses in breast cancer. Plos One 2012;7(11):e48788.

Hsu WL, Lin HY, Chiou SS, Chang CC, et al. House mammary tumor virus-like nucleotide sequences in canine and feline mammary tumors. J Clin Microbiol 2010;48(12):4354-62.

Johal H, Faedo M, Faltas J, et al. DNA of mouse mammary tumor virus-like virus is present in human tumors influenced by hormones. J Med Virol 2010;82(6):1044-50.

Kar SP, Beesley J, Amin AI Olama A, et al. Genome-wide meta-analyses of breast, ovarian, and prostate cancer association studies identify multiple new susceptibility loci shared by at least two cancer types. Cancer Discov 2016;6(9):1052-67.

Khan NA, Castillo A, Koriyama C, et al. Human papillomavirus detected in female breast carcinomas in Japan. Br J Cancer 2008;99(3):408-14.

Labrecque LG, Barnes DM, Fentiman IS, Griffin BE. Epstein-Barr virus in epithelial cell tumors: a breast cancer study. Cancer Res 1995;55(1):39-45.

Latif N, Rana F, Guthrie T. Breast cancer and HIV in the era of highly active antiretroviral therapy: two case reports and review of the literature. Breast j 2011;17(1):87-92.

Laumbacher B, Fellerhoff B, Herzberger B, et al. Do dogs harbour risk factors for human breast cancer? Med Hypotheses 2006;67(1):21-6. Epub Mar. 3, 2006.

Lawson JS, Mazzanti C, Civita P, et al. Association of mouse mammary tumor virus with human breast cancer: histology, immunohistochemistry and polymerase chain reaction analyses. Front Oncol 2018;8:141.

Lawson JS, Salmons B, Glenn WK. Oncogenic viruses and breast cancer: Mouse Mammary Tumor Virus (MMTV), Bovine Leukemia Virus (BLV), Human Papilloma Virus (HPV), and Epstein-Barr Virus (EBV). Front Oncol 2018;8:1.

Lawson JS, Glenn WK. Multiple oncogenic viruses are present in human breast tissues before development of virus associated breast cancer. Infect Agent Cancer 2017;12:55.

Liu B, Wang Y, Melana SM, et al. Identification of a proviral structure in human breast cancer. Cancer Res 2001;61(4):1754-9.

Vadlapatla RK, Pal D, Vadlapudl AD et al. Ritonavir: A powerful boosting agent for overcoming drug resistance in cancer chemotherapy. Cancer Sci Ther 2014,6:11.

Mazzanti CM, Lessi F, Armogida I, et al. Human saliva as route of inter-human infection for mouse mammary tumor virus. Oncotarget 2015;6(21):18355-63.

Melana SM, Holland JF, Pogo BG. Search for mouse mammary tumor virus-like env sequences in cancer and normal breast from the same individuals. Clin Cancer Res 2001;7(2):283-4.

Melana SM, Nepomnaschy I, Sakalian M, et al. Characterization of viral particles isolated from primary cultures of human breast cancer cells. Cancer Res 2007;67(18):8960-5.

Moore R, Dixon M, Smith R, Peters G, Dickson C. Complete nucleotide sequence of a milk-transmitted mouse mammary tumor virus: two frameshift suppression events are required for translation of gag and pol. J Virol 1987;61 (2):480-90.

Nartey T, Mazzanti CM, Melana S, et al. Mouse mammary tumor-like virus (MMTV) is present in human breast tissue before development of virally associated breast cancer. Infect Agent Cancer 2017;12:1.

Nartey T, Moran H, Marin T, et al. Human mammary tumor virus (HMTV) sequences in human milk. Infect Agent Cancer 2014;9:20.

Ohba K, Ichiyama K, Yajima M, et al. In vivo and in vitro studies suggest a possible involvement of HPV infection in the early stage of breast carcinogenesis via APOBEC3B induction. Plos One 2014;9(5):e97787.

Wang Y, Holland JF, Bleiweiss IJ, et al. Detection of mammary tumor virus env gene-like sequences in human breast cancer. Cancer Res 1995;55(22):5173-9.

Wei WZ, Gill RF, Wang H. Mouse mammary tumor virus associated antigens and superantigens—immuno-molecular correlates of neoplastic progression. Semin Cancer Biol 1993;4(3):205-13.

Weiss, RA. Retrovirus classification and cell interactions. J Antimicrob Chemother 1996;37. Suppl B:1-11. Review.

Bell T. Isolation of a reovirus from a case of Burkitt's lymphoma. Brit Med J, 1964. 1: 1212.

Andersson A. Expression of human endogenous retrovirus ERV3 (HERV-R) mRNA in normal and neoplastic tissues. Int J Onc, 1998. 12: 309-313.

Benit L. Identification, Phylogeny, and Evolution of Retroviral Elements Based on Their Envelope Genes. J Virology, 2001. 75: 23, 11709-11719.

Bera T. Defective Retrovirus Insertion Activates c-Ha-ras Proto-oncogene in an MNU—Induced Rat Mammary Carcinoma. Biochem Biophy Res Comm, 1998. 248: 835-840.

Berkhout B. Identification of an Active Reverse Transcriptase Enzyme Encoded by a Human Endogenous HERV-K Retrovirus. J Virology, 1999. 73: 3, 2365-2375.

Bindra A. Search for DNA of exogenous mouse mammary tumor virus-related virus in human breast cancer samples. J Gen Virol, 2007. 88: 1806-1809.

Bittner J. Some Possible effects of nursing on the mammary gland tumor incidence in mice. Science, Aug. 14, 1936. 84: 162.

Bittner J. The Milk-Influence of Breast Tumors in Mice. Science, May 1, 1942. 95:462-463.

Blair P. Neutralization of the mouse mammary tumor virus by rabbit antisera against C3Hf tissue. Cancer Res, 1963. 23: 381.

Bock M. Endogenous retroviruses and the human germline. Current Opinions in Genetics & Development, 2000. 10: 651-655.

Day N. Antibodies reactive with murine mammary tumor virus in sera of patients with breast cancer: Geographic and family studies. Proc Natl Acad Sci USA, 1981. 78:2483-2487.

Dion A. A human protein related to the major envelope protein of murine mammary tumor virus: identification and characterization. Proc Natl Acad Sci USA. 1980. 77: 1301-1305.

Dmochowski L. The milk agent in the origin of mammary tumors in mice. Adv Cancer Res. 1953. 1:103.

Epstein M. Morphological and biological studies on a virus in cultured lymphoblasts from Burkitt's lymphoma. J Exp Med. 1965. 121:761.

Ekbom A. Breast-feeding and breast cancer in the offspring. British J. Cancer, 1993. 67: 2375-2382.

Etkind P. Mouse mammary tumor virus-like ENV gene sequences in human breast tumors and in a lymphoma of a breast cancer patient. Clin Can Res 2000. 6: 1273-78.

Etkind P. Clonal isolation of different strains of mouse mammary tumor virus-like DNA sequences from both the breast tumors and non-Hodgkin's lymphomas of individual patients diagnosed with both malignancies. Clin Cancer Res 2004. 10: 5656-5664.

Faedo M. Mouse mammary tumor-like virus is associated with p53 nuclear accumulation and progesterone receptor positivity but not estrogen positivity in human female breast cancer. Clin Cancer Res. 2004. 10: 4417-4419.

Fennelly J. Co-amplification of tail-to-tail copies of MuRVY and APE retroviral genomes on the Mus musculus Y Chromosome. Mammalian Genome, 1996, 7: 31-36.

Fernandez-Cobo M. Transcription profiles of non-immortalized breast cancer cells. Biomed Central Cancer, 2006. 6: 99-100.

Ford C. Mouse mammary tumor virus-like gene sequences in breast tumors of Australian and Vietnamese women. Clin Cancer Res, 2003. 9: 1118-1120.

Ford C. MMTV virus-like RNA transcripts and DNA are found in affected cells of human breast cancer. Clin Cancer Res. 2004. 10: 7284-7289.

Franklin G. Expression of Human Sequences Related to Those of Mouse Mammary Tumor Virus. Journal of Virology, 1988. 62:1203-1210.

Friedman G. Spousal concordance for cancer incidence. A cohort study. Cancer, 2000. 86: 2413-2419.

(56) References Cited

OTHER PUBLICATIONS

Fukuoka H. No association of mouse mammary tumor virus-related retrovirus with Japanese cases of breast cancer. J Med Virol. 2008. 80: 1447-1451.
Golovkina T. Coexpression of Exogenous and Endogenous Mouse Mammary Tumor Virus RNA In Vivo Results in Viral Recombination and Broadens the Virus Host Range. Journal of Virology, 1994. 68:5019-5026.
Golovkina, T. A novel membrane protein is a mouse mammary tumor virus receptor. J. Virol. 1998. 72:3066-71.
Gotlieb-Stematsky T. Increased tumor formation by polyoma virus in the presence of non-oncogenic viruses. Nature, 1966. 212: 421.
Gray D. Activation of int-1 and int-2 Loci in GRf Mammary Tumors. Virology, 1986. 154: 271-278.
Griffiths D. Endogenous retroviruses in the human genome sequence. Genome Biology, 2001. 2: 6, 1017.1-1017.5.
Hachana M. Prevalence and characteristics of the MMTV-like associated breast carcinomas in Tunisia. Cancer Lett. 2008. 271: 222-230.
Held W. Reverse Transcriptase-dependent and -independent Phases of Infection with Mouse Mammary Tumor Virus: Implications for Superantigen Function. J Exp Med, 1994. 180:2347-2351.
Heller J. Research on cancer viruses. Public Health Rep. 1960. 75:501.
Howard D. Isolation of a series of novel variants of murine mammary tumor viruses with broadened host range. Int J. Cancer, 1980. 25:647-654.
Hughes J. Evidence for genomic rearrangements mediated by human endogenous retroviruses during primate evolution. Nature Genetics, 2001. 29: 487-489.
Imai S. Distribution of Mouse Mammary Tumor Virus in Asian Wild Mice. Journal of Virology, 1994. 68:3437-3442.
Identity crisis. Nature, 2009. 457: 935-936, Indik S. Mouse mammary tumor virus infects human cells. Cancer Res, 2005. 65: 6651-6659.
Indik S. A novel, mouse mammary tumor virus encoded protein with Rev-like properties. Virology, 2005. 337: 1-6.
Indik S. Rapid spread of mouse mammary tumor virus in cultured human breast cells. Retrovirology, 2007. 4: 73.
Karlsson H. Retroviral RNA identified in the cerebrospinal fluids of brains of individuals with schizophrenia. PNAS, 2001. 98: 8, 4634-4639.
Katz E. MMTV env encodes an ITAM responsible for transformation of mammary epithelial cells in three-dimensional culture. J Exp Med, 2005. 201: 431-439.
Kidd J. The enduring partnership of a neoplastic virus and carcinoma cells. Continued increase of virus in the V2 carcinoma during propagation in virus immune hosts. J Exp Med. 1942. 75:7.
Lawson J. From Bittner to Barr: a viral, diet and hormone breast cancer aetiology hypothesis. Breast Cancer Res, 2001. 3:81-85.
Leib C. Endogenous Retroviral Elements in Human DNA. Cancer research (Supp), 1990. 50:5636-5642.
Levine P. Increased incidence of mouse mammary tumor virus-related antigen in Tunisian patients with breast cancer. Int. J. Cancer, 1984. 3:305-308.
Nusse et al., "Localization of a Gene for Expression of Mouse Mammary Tumor Virus Antigens in the GR/Mtv2-Mouse Strain", J. Exp. Med, The Rockefeller University Press, vol. 152, Sep. 1980, pp. 712-719.
International Search Report dated Nov. 19, 2019 in corresponding PCT Application No. PCT/US2019/40361.
Corresponding PCT International Search Report and Written Opinion dated Nov. 19, 2020.
drugs.com; Ritonavir Dosage; Publication online Mar. 28, 2019.
Lytvyak et al.; World Journal of Gastroenterology; Combination Antiretroviral Studies for Patients with Primary Biliary Cirrhosis; Jan. 7, 2016.
drugs.com; Atazanavir Dosage; Apr. 15, 2019.
Braitbard, et al.; A new immunization and treatment strategy for mouse mammary tumor virus; Feb. 26, 2016.

\* cited by examiner

SEQUENCE LISTING

```
<160> NUMBER OF SEQ ID NOS: 2

<210> SEQ ID NO 1
<211> LENGTH: 590
<212> TYPE: PRT
<213> ORGANISM: Mammary Tumor Virus

<400> SEQUENCE: 1

Gly Val Ser Gly Ser Lys Gly Gln Lys Leu Phe Val Ser Val Leu Gln
1               5                   10                  15

Arg Leu Leu Ser Glu Arg Gly Leu His Val Lys Glu Ser Ser Ala Ile
                20                  25                  30

Glu Phe Tyr Gln Phe Leu Ile Lys Val Ser Pro Trp Phe Pro Glu Glu
            35                  40                  45

Gly Gly Leu Asn Leu Gln Asp Trp Lys Arg Val Gly Arg Glu Met Lys
        50                  55                  60

Arg Tyr Ala Ala Glu His Gly Thr Asp Ser Ile Pro Lys Gln Ala Tyr
65                  70                  75                  80

Pro Ile Trp Leu Gln Leu Arg Glu Ile Leu Thr Glu Gln Ser Asp Leu
                85                  90                  95

Val Leu Leu Ser Ala Glu Ala Lys Ser Val Thr Glu Glu Leu Glu
                100                 105                 110

Glu Gly Leu Thr Gly Leu Leu Ser Thr Ser Ser Gln Glu Lys Thr Tyr
            115                 120                 125

Gly Thr Arg Gly Thr Ala Tyr Ala Glu Ile Asp Thr Glu Val Asp Lys
        130                 135                 140

Leu Ser Glu His Ile Tyr Asp Glu Pro Tyr Glu Glu Lys Glu Lys Ala
145                 150                 155                 160

Asp Lys Asn Glu Glu Lys Asp His Val Arg Lys Ile Lys Lys Val Val
                165                 170                 175

Gln Arg Lys Glu Asn Ser Glu Gly Lys Arg Lys Glu Lys Asp Ser Lys
            180                 185                 190

Ala Phe Leu Ala Thr Asp Trp Asn Asp Asp Leu Ser Pro Glu Asp
        195                 200                 205

Trp Asp Asp Leu Glu Glu Gln Ala Ala His Tyr His Asp Asp Glu
    210                 215                 220

Leu Ile Leu Pro Val Lys Arg Lys Val Val Lys Lys Pro Gln Ala
225                 230                 235                 240

Leu Arg Arg Lys Pro Leu Pro Pro Val Gly Phe Ala Gly Ala Met Ala
                245                 250                 255

Glu Ala Arg Glu Lys Gly Asp Leu Thr Phe Thr Phe Pro Val Val Phe
            260                 265                 270

Met Gly Glu Ser Asp Glu Asp Thr Pro Val Trp Glu Pro Leu Pro
        275                 280                 285
```

-continued

Leu Lys Thr Leu Lys Glu Leu Gln Ser Ala Val Arg Thr Met Gly Pro
    290                 295                 300

Ser Ala Pro Tyr Thr Leu Gln Val Val Asp Met Val Ala Ser Gln Trp
305                 310                 315                 320

Leu Thr Pro Ser Asp Trp His Gln Thr Ala Arg Ala Thr Leu Ser Pro
                325                 330                 335

Gly Asp Tyr Val Leu Trp Arg Thr Glu Tyr Glu Lys Ser Lys Glu
                340                 345                 350

Met Val Gln Lys Ala Ala Gly Lys Arg Lys Gly Lys Val Ser Leu Asp
                355                 360                 365

Met Leu Leu Gly Thr Gly Gln Phe Leu Ser Pro Ser Ser Gln Ile Lys
370                 375                 380

Leu Ser Lys Asp Val Leu Lys Asp Val Thr Thr Asn Ala Val Leu Ala
385                 390                 395                 400

Trp Arg Ala Ile Pro Pro Gly Val Lys Lys Thr Val Leu Ala Gly
                405                 410                 415

Leu Lys Gln Gly Asn Glu Glu Ser Tyr Glu Thr Phe Ile Ser Arg Leu
                420                 425                 430

Glu Glu Ala Val Tyr Arg Met Met Pro Arg Gly Glu Gly Ser Asp Ile
                435                 440                 445

Leu Ile Lys Gln Leu Ala Trp Glu Asn Ala Asn Ser Leu Cys Gln Asp
450                 455                 460

Leu Ile Arg Pro Ile Arg Lys Thr Gly Thr Ile Gln Asp Tyr Ile Arg
465                 470                 475                 480

Ala Cys Leu Asp Ala Ser Pro Ala Val Val Gln Gly Met Ala Tyr Ala
                485                 490                 495

Ala Ala Met Arg Gly Gln Lys Tyr Ser Thr Phe Val Lys Gln Thr Tyr
                500                 505                 510

Gly Gly Gly Lys Gly Gly Gln Gly Ala Glu Gly Pro Val Cys Phe Ser
                515                 520                 525

Cys Gly Lys Thr Gly His Ile Arg Lys Asp Cys Lys Asp Glu Lys Gly
                530                 535                 540

Ser Lys Arg Ala Pro Pro Gly Leu Cys Pro Arg Cys Lys Lys Gly Tyr
545                 550                 555                 560

His Trp Lys Ser Glu Cys Lys Ser Lys Phe Asp Lys Asp Gly Asn Pro
                565                 570                 575

Leu Pro Pro Leu Glu Thr Asn Ala Glu Asn Ser Lys Asn Leu
                580                 585                 590

<210> SEQ ID NO 2
<211> LENGTH: 98
<212> TYPE: PRT
<213> ORGANISM: Mammary Tumor Virus

<400> SEQUENCE: 2

Gly Val Ser Gly Ser Lys Gly Gln Lys Leu Phe Val Ser Val Leu Gln
1               5                   10                  15

Arg Leu Leu Ser Glu Arg Gly Leu His Val Lys Glu Ser Ser Ala Ile
                20                  25                  30

Glu Phe Tyr Gln Phe Leu Ile Lys Val Ser Pro Trp Phe Pro Glu Glu
            35                  40                  45

Gly Gly Leu Asn Leu Gln Asp Trp Lys Arg Val Gly Arg Glu Met Lys
        50                  55                  60

Arg Tyr Ala Ala Glu His Gly Thr Asp Ser Ile Pro Lys Gln Ala Tyr
65                  70                  75                  80

```
Pro Ile Trp Leu Gln Leu Arg Glu Ile Leu Thr Glu Gln Ser Asp Leu
            85                  90                  95
Val Leu
```

MAMMARY TUMOR VIRUS VACCINE

SUBMISSION OF SEQUENCE LISTING ON ASCII TEXT FILE

The instant application contains a Sequence Listing which has been submitted electronically in ASCII format and is hereby incorporated by reference in its entirety. Said ASCII file, created on Jul. 29, 2019, is named 1133-0002-SL-CORRECTED.txt and is 6,212 bytes in size. The content of the ASCII text file incorporated herein by reference is a computer readable form (CRF) of two sequences:

SEQ. 1 Illustrates an example Pr75gag polyprotein sequence.
SEQ. 2 Illustrates an example transitional protein p10 sequence.

BACKGROUND

Technical Field

Embodiments of the invention generally fall into the category of vaccinations. Other embodiments of the invention generally fall into the category of synthetic virus peptides or viral proteins used in a vaccination. In some embodiments a natural virus, a component of the natural virus, or a synthetic virus particle or protein created from mammary tumor virus components is used to elicit an immune response, generating a protective response to exposure to the mammary tumor virus. In another embodiment, synthetic virus proteins are created to form a multi-component vaccine.

Discussion of Art

The etiology of breast cancer is likely multi-factorial. Genetics are known to play a role (BRCA for example), as do diet, and hormones (Dudley, 2016). The mammary tumor virus (MTV) is found across a broad range of species, mammals in particular. The virus is implicated as a general tumor-forming virus, suggesting that it may well be a wide-ranging zoonotic tumor virus with deep penetration throughout our shared environment. The Mouse Mammary Tumor Virus (MMTV) was first described by Bittner in 1936, in the context of its being an exogenous infectious agent that was transmitted from mother mouse to baby mouse through breastmilk. Weiss later categorized it as a B type retrovirus, comparable to HIV, but carried in far smaller concentrations (1996). As a B type retrovirus, MMTV belongs to a group globally recognized as being oncogenic. As such, it acts through insertional mutagenesis, ultimately producing a tumor in its target tissue.

MMTV strains vary according to species of mouse, which itself varies by geography and historical custom. The observance of the parallel trends in MMTV expression and human breast cancer lead to a probable associative link between the two. Areas that have higher concentrations of rodents and have had them for a longer period of time show increased virulence and increased rates of cancer. In fact, the incidence and manifestation of breast cancer in humans can be directly correlated to the species of mouse endemic to a given area. Regions where mouse populations are generally low, like East Asia, have lower overall breast cancer rates, and those populations have tumors that exhibit very low virus positivity (Khan, 2008; San, 2017). The most virulent strains of MMTV lie in the Middle East, an area with a higher rodent population and where breast cancer onset and severity are more pronounced than elsewhere (Chouchane, 2013). In the United States and Mexico, where mice are ubiquitous, tumor samples test positive for the MMTV virus (Cedro, 2014) and can be linked to the "house mouse," mus domesticus (Stewart, 2000).

Figure 1:
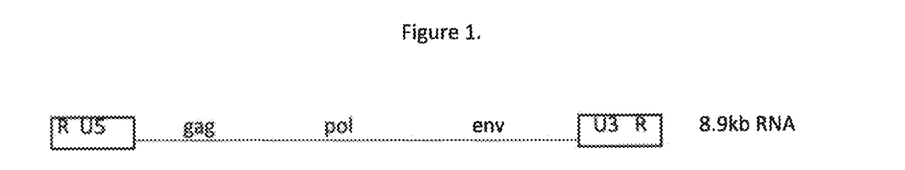
FIG. 1 Illustrates the general generic genomic structure of a generic MTV.

A hormonally-activated and regulated retrovirus, the genetic code of MTV is fully deciphered for variants found in some mammalian species. The genetic code of the deciphered variants shares a common genetic architecture with many other retroviruses with major expression groups comprising: long terminal repeats (LTR); group antigen polyproteins (GAG); reverse transcriptases and polymerases (POL); and, envelope proteins (ENV). FIG. 1 provides an illustration of this generalized architectural structure for MTV. The proteins that compose the GAG group generally form the viral core structure, RNA genome binding proteins, and are the major proteins comprising the nucleoprotein core. The GAG group may also encode viral matrix, capsid, and nucleoproteins. The POL reverse transcriptase is the essential enzyme that carries out the reverse transcription process that takes the viral RNA genome to a double-stranded DNA preintegrated form. The ENV group encodes for host cell transmembrane and surface-receptor subunits, and regulatory subunits found on the endoplasmic reticulum of the host cell in addition to the proteins that form the viral envelope.

The MMTV virus, while endemic to mice, appears to be acquired within the species itself. An antigenic component, the GP52 envelope protein can reliably be found in the blood and reproductive organs of infected mice (Arthur, 1978), as can antibodies to envelope proteins such as GP52. The virus is passed through breast milk, urine, feces, and/or saliva, and it travels liberally until it finds hormone-dependent tissues to infect, with breast being the preferred target. Once inside a cell, the virus randomly inserts into a series of integration sites (Faschinger, 2008), ultimately meeting an oncogene and producing the necessary frameshift to cause a cancer-producing mutation (Moore, 1987).

Due to the apparent connection between MMTV exposure and breast cancer in mice, coupled with the above mouse population-human breast cancer prevalence observations, many efforts have been made to find a human correlate to the virus, the Human Mammary Tumor Virus (HMTV), and its subsequent role in breast cancer in women. A human corollary found to be 85-95% homologous to MMTV was described by Melana and Holland in 2001. This HMTV was identified in human breast cancer specimens, first through identification of MMTV envelope proteins (Wang, 1995) and later with the discovery of proviral units specific to human subjects (Liu, 2001).

While the prevalence of HMTV in breast cancer tissue has varied widely across studies, there is evidence that it is consistently well-represented in certain types of cancers, namely ductal carcinoma in situ (DCIS; Mazzanti, 2011). Even in subjects with significant disease, the virus may be somewhat elusive, owing to the fact that it is present in low concentrations (Bindra, 2007), and serves as a relatively remote precursor to oncogenesis (Nartey, 2017). Viral acquisition predates tumor formation by one to eleven years (Lawson, 2017), with the virus itself possibly becoming less virulent after initial mutagenesis. Ultimately, viral particles can be detected in tumor tissue and breast milk (Nartey, 2014), demonstrating a predilection for that organ system. The affinity for breast tissue includes male subjects as well, in whom particles have been isolated from benign cases of gynecomastia (Ford, 2004).

HMTV shares homology with MMTV in both form and action and the two share similar genetic sequences. Human breast tumors demonstrate evidence of envelope protein units, as well as equivalent RNA segments known to originate from MMTV (Axel, 1962). The HMTV virus inserts similarly into the genome at random sites, ultimately inciting comparable mutations by activating various oncogenes (Callahan, 2012). Representatives of the envelope protein can be localized to the host cell membrane, but are more prominent in cellular cytoplasm (Tomana, 1981).

In general, transcription processes read through an MTV genome and mRNA is polyadenylated and processed using signals in transcribed regions from the 3' LTR at the end of the transcribed RNA. The full-length message can be spliced to lead to production of envelope proteins (or other proteins depending upon retroviral class). Unspliced full-length mRNA can give rise to GAG-POL precursor poplyproteins. Alternatively, GAG and POL proteins, and other MTV proteins, or protein subunits may first arise from translated mRNA polypeptide precursor molecules. Multiple precursors are possible and may contain multiple proteins or protein subunits. A viral protease cleaves the precursor into multiple subunits with varying functions. An ENV protein complex, for example, may be translated from mRNA segments into multiple precursors which are then cleaved by endogenous proteases to yield multiple subunits that assemble into a mature surface glycoprotein.

Translated proteins assemble a retroviral particle at the host cell surface. Full-length genomic unspliced mRNA (containing a packaging signal termed Psi) is bound by GAG-derived proteins and incorporated into the budding particle. As a B-type retrovirus the general structure of a mature MTV particle is characterized by prominent surface protein "spikes" and a dense acentric nucleocapsid.

There are many types of vaccines, categorized by the antigen used in their preparation. Their formulations affect how they are used, how they are stored, and how they are administered. There are at least four main types of vaccine: Live Attenuated Virus ("LAV"), Inactivated (killed antigen), Subunit (purified antigen), and Toxoid (inactivated toxins). Vaccines may be monovalent of polyvalent. A monovalent vaccine contains a single strain of a single antigen (e.g. Measles vaccine), whereas a polyvalent vaccine contains two or more strains/serotypes of the same antigen (e.g. OPV). Some of the antigens above can be combined in a single injection that can prevent different diseases or that protect against multiple strains of infectious agents causing the same disease (e.g. combination vaccine DPT combining diphtheria, pertussis and tetanus antigens). Thus, combination vaccines can be useful to overcome the logistic constraints of multiple injections and accommodate for a child's fear of needles and pain. As used in this application, the term "polyvalent vaccine" refers to multiple antigen types that may derive from a single or multiple disease vectors whereas a "combination vaccine" refers to a vaccine with multiple antigens targeting at least two or more diseases. Thus, a "polyvalent vaccine" may have multiple antigens but only provide immunity to a single disease whereas a "combination vaccine" may contain a single type of antigen from two or more disease vectors and give rise to an immunity for those two or more diseases.

Available since the 1950s, live attenuated vaccines (LAV) are derived from disease-causing pathogens (virus or bacteria) that have been weakened under laboratory conditions. They will grow in a vaccinated individual, but because they are weak, they will cause no or very mild disease. Inactivated vaccines are made from microorganisms (viruses, bacteria, other) that have been killed through physical or chemical processes. These killed organisms cannot cause disease.

Subunit vaccines, like inactivated whole-cell vaccines do not contain live components of the pathogen. They differ from inactivated whole-cell vaccines, by containing only the antigenic parts of the pathogen. Protein based subunit vaccines present an antigen to the immune system without viral particles, using a specific, isolated protein of the pathogen. Some bacteria when infecting humans are often protected by a polysaccharide (sugar) capsule that helps the organism evade the human defense systems especially in infants and young children. Polysaccharide vaccines create a response against the molecules in the pathogen's capsule. Conjugate subunit vaccines also create a response against the molecules in the pathogen's capsule. In comparison to plain polysaccharide vaccines, they benefit from a technology that binds the polysaccharide to a carrier protein that can induce a long-term protective response.

Toxoid vaccines are based on the toxin produced by certain bacteria (e.g. tetanus or diphtheria). The toxin invades the bloodstream and is largely responsible for the symptoms of the disease. The protein-based toxin is rendered harmless (toxoid) and used as the antigen in the vaccine to elicit immunity. To increase the immune response, the toxoid is often adsorbed to aluminum or calcium salts, which serve as adjuvants.

The discovery of Human Endogenous Retroviruses (HERV) DNA sequences embedded in the genome has led to the hypothesis that many retroviruses, or genetic elements derived from retroviruses, are now endogenous to humans; the result of many generations of people being repeatedly exposed to the agents and eventually integrating them into their DNA. The HERV equivalent to MTV has been found in human subjects (Salmon, 2014). Some researchers hypothesize that HMTV is purely endogenous, and that efforts at curtailing its oncogenic potential should be directed at genetic manipulation rather than immunization against an exogenous entity (Yang, et al., 1987).

MTV behaves in a fashion more consistent as an exogenous particle (Ford, 2004; Melana, 2007). The fact that the virus is acquired up to ten years prior to disease onset in view of the fact that the mean age of onset of breast cancer is over 50 leads the argument for an endogenous factor to fall short. Furthermore, the measured immunogenicity against MTV is consistent with that of an acquired infection, and is maximal during disease latency (Black, 1976).

In the setting of MTV and its probable role in breast cancer, there is strong evidence in support of a combinatorial effect of MTV with multiple oncogenic viruses acting in conjunction and potentiating each other during tumorigenesis (Corbex, 2014; Glenn, 2012; Lawson, 2018; Al Moustafa, 2016). Taken as a whole, the data on MTV suggests that there are in fact endogenous and exogenous versions of the virus, many with little clinical relevance to immediate disease. It is also probable that the HERVs previously described represent remnants of prior integrations, and that newer incidences of MTV infection ultimately lead to cancer onset.

Efforts at measuring MTV antibodies have had varying success. Antibodies to some envelope proteins have been isolated, although sparingly, as they seem to wane with disease progression as previously mentioned. The MTV virus itself also appears to have evolved mechanisms that blunt the host response to infection (Dudley, 2016). Previous diagnostic tests for MTV in humans have been limited to localizing the envelope protein in the host, as opposed to finding the more prevalent and longer lasting intracellular elements. (Holland, 1995)

While mice are ubiquitous and are known to be present in both homes and food storage facilities, MTV appears to require more intimate contact for effective transmission. Various efforts to detect MTV in other species have shown that correlates are found in primates, feline and canine species, in addition to the well-known mouse model (Szabo, 2005). Across-species transmission is possible, as evidenced by the acquisition of MMTV in lab personnel who performed frequent handling of infected mice (Dion, 1986).

MTV appears to require repeated and frequent exposure for effective transmission. To that end, domesticated pets have become the prime targets for study, and the prime suspects as vectors. MTV particles are found in the non-cancer cells of house pets, with sequences similar to those of infected mice (Hsu, 2010). Pet-human interaction being frequent and extensive, studies have then proceeded to identify the most common mode of transmission between them. Given that MTV has been detected in various body fluids, saliva was next to be evaluated for its virulent potential.

In 2015, Mazzanti identified MMTV particles in human saliva, suggesting that to be one mode of transmission between humans. Extrapolating from that data, it is likely that the house pets in whom MTV variants are found also have the virus present in their saliva, and pet saliva itself is ubiquitous in human homes. Dog ownership in particular has been isolated as an independent risk factor for breast cancer in women (Laumbacher, 2006), a fact anecdotally replicated on a daily basis in oncologic surgery practices in the United States.

Finally, given the above putative associations between MTV and cancer there have been past attempts at creating an MTV vaccine. However, the prior attempts at generating an MTV vaccine have used ENV proteins or protein parts and failed to raise the required immune response. Thus, there is a need for an MTV vaccine capable of inducing immunity in humans and in human-associated animals.

BRIEF SUMMARY OF THE INVENTION

An embodiment of the invention is a vaccine comprising an MTV transition protein.

Another embodiment of the invention is a vaccine comprising MTV polypeptides coupled to a carrier protein.

Another embodiment of the invention is a method of treating MTV comprising, providing an MTV vaccine with an MTV transition protein; and, administering said vaccine.

BRIEF DESCRIPTION OF THE DRAWINGS

Features and advantages of embodiments of the present invention will become apparent on reading the detailed description below with reference to the drawings, which are illustrative but non-limiting, wherein.

DETAILED DESCRIPTION OF THE INVENTION

Although described above as singular genetic elements, each class of ENV, GAG, POL, and LTR, may encode for multiple proteins, subunits, glycosylation sites, or signaling factors. Vaccines also include a variety of ingredients besides classifying antigens and can include: stabilizers, adjuvants, antibiotics, and preservatives. In this instance the term "vaccine" is used as ordinarily understood and may also contain a secondary descriptor describing the antigenic component eliciting the desired immune response along with the associated ingredients tailored to the desired effect. Thus, a live vaccine can have different associated ingredients than a subunit-based vaccine. Both are vaccines and raise an immune response but with different antigens. Or, in the alternative, two live vaccines may have the same antigen but varied ingredients (e.g., in response to administration requirements). Or, in other embodiments, the vaccine may have the same antigen (e.g., an ENV protein or protein subunit) that is derived from one or more sources (e.g., an ENV protein from a human and one from a cat). In other embodiments, two or more antigenic components may be combined to increase immune system response greater than an individual antigen alone (e.g., an ENV protein combined with a protein precursor). Additionally, antigens for MTV may be combined with other antigens for other diseases into a mono or poly-valent combination vaccine.

The term "antigens" and derivatives are defined as the components typically derived from the structure of disease-causing organisms, which are recognized as "foreign" by the immune system and trigger a protective immune response to the vaccine. Importantly, the antigen component does not have to be made by the disease-causing organism in order to be used. For example, viral proteins or protein precursors may be manufactured and purified using bacterial or fungal systems in bulk and then purified for use in a vaccine serum.

Vaccines may be administered through multiple routes at least including: intramuscular injection, subcutaneous injection, intradermal injection, orally, or through intranasal sprays. It is understood that each route of administration may require its own mix of antigens and associated ingredients.

In this application synthetic proteins and derivatives are prefixed with an "syn" such as synMTV or synENV, synPOL, etc. to differentiate from naturally occurring versions. For example, an synENV protein may be derived from a genetic sequence identical to or modified from (e.g., introns removed, different starter code and reading frame, different promoters etc.) a naturally occurring sequence but produced in an alternative system of protein expression (e.g., in yeast or e. coli, etc.). Likewise, the amino acid sequences, and underlying genetics, for each protein may vary across viral sub-species found in different mammalian species. synProteins or synProtein subunits (such as those produced by a protein cleavage process, those produced by restriction processes, or those produced by artificial amino-acid peptide chain construction, amino acid printing, or other artificial systems or protein or protein product expression) may be derived in whole or in part from single or multiple viral sub-types (e.g., human sequence synProtein combined with canine synProtein to form a polyvalent vaccine protective against both HMTV and canine MTV virus particles).

In an example embodiment, an engineered vaccine is created by synthesizing and purifying an EP3-p14-p10 peptide chain. The peptides, in haptan formulation, are coupled to keyhole limpet hemocyanin (KLH) and extensively dialyzed. Moles of conjugated peptide/mole of KLH are determined by amino acid analysis and range between 700 and 1,000. Positive and negative controls consist of gp52, purified from C3H-MMTV and a scrambled peptide sequence coupled to KLH respectively. Still other embodiments may employ different carrier proteins including at least: Concholepas concholepas hemocyanin, bovine serum albumin (BSA), cationized BSA, or ovalbumin, and any other carrier proteins. In still another embodiment, multiple antigens, for instance from other viral-mediated cancers or tumor-associated antigens, or for other diseases which may be vaccinated against, may also be attached to one or more carrier proteins and combined to form a polyvalent combination vaccine.

The MTV envelope (ENV) class of proteins is known to have conserved elements across variants of the virus detected across multiple species. In particular, the ENV proteins may comprise those that are signaling peptides, those that are specific to the outer membrane of the virus particle, those specific to the endoplasmic reticulum, and those that are trans-membrane anchors. The polymerase (POL) protein class may comprise both a polymerase and/or a reverse transcriptase and an associated signaling factor. The group antigen (GAG) proteins form the viral core structure, RNA genome binding proteins, and are the major proteins comprising the nucleoprotein core particle. The POL and GAG group proteins are likewise thought to have conserved cross-species elements.

Without subscribing or limiting to any specific theory or practice, variants within and between the above genetic motifs may account for viral traits such as specificity, genetic integration location, surface protein structures, species specificity, etc. Thus, by altering combinations one may target a vaccine to protect against an MTV exposure in various species. This may be accomplished by either deriving a viral subspecies from the target species of interest or utilizing synProteins or synProtein subunits derived from species-specific sequence data. A target species may be one whose MTV viral protein sequences differ enough from the primary MTV antigen in a vaccine that a separate antigen is required to raise or enhance an immune response either in the species of interest or to increase an immune response, for example in a human, in reaction to an exposure of an MTV variant from the target species. For example, a human MTV vaccine with a transition protein may include additional MTV polypeptide antigens whose sequences are derived from human companion species such as a dog, cat, ferret, etc. Thus, while the vaccine may also possibly be administered to the human-companion animal to reduce viral load in the animal (and hence exposure to the human), the additional MTV component also strengthens the immune response of the human to the target species variant of MTV.

Accordingly, another embodiment of the invention comprises an MTV vaccine derived from attenuated or inactivated MTV particles derived from either single or multiple species. Other embodiment vaccines are derived from synProteins and synProtein subunits of the ENV, POL, and GAG protein classes. An additional embodiment is composed of synProteins and/or synProtein subunits derived from cross-species conserved sequences. For example, some portions of the sequence of the gp52 ENV protein are known to be conserved across MTV variants. Thus, an synProtein subunit based on the conserved sequence could be used in a vaccine to induce immunity to MTV in multiple species, including human-associated animals such as dogs, cats, and other human-companion animals or increase the immune response in a human to MTV variants derived from the animals.

In still another example embodiment, a purified MTV virus from one or multiple species is combined with 1.2× $10^{-2}$ M formalin for a concentration of 1:3,000 formaldehyde. It is then incubated in the dark at 4° C. for 5 days (or room temperature for 72 h) and stored at 4° C. It is diluted to contain 50 ng protein $\mu l^{-1}$ and emulsified with an equal volume of complete Freund's adjuvant (CFA). The preparation is then stored at −70° C. until used. In some embodiments the above serum is combined with or more additional vaccine sera to form polyvalent, compound, or compound polyvalent vaccines targeted at one or more additional diseases.

In another example embodiment, MTV virus particles from one or multiple species may be subjected to fragmentation processes designed to break apart the virus into multiple protein and protein pieces (e.g., sonication, vibration, freeze-fracture, etc.). MTV proteins and/or protein subunits may then be collected, purified, and fixed in a vaccine preparation. Particular preparations may include purified ENV, POL, or GAG proteins or protein subunits. In a further embodiment the purified proteins may include p10, p14, and gp52.

As briefly outlined above, RNA viruses in many families and genera express their genomes in ways which involve the synthesis and subsequent cleavage of polypeptide chains known as precursor polyproteins. This stratagem allows the activation of subsets of proteins with different biochemical functions from the same precursor polyprotein. Although the virus-encoded enzymes responsible for processing the polyproteins are structurally diverse, they are all highly specific for their substrates. The resulting processing cascade is a tightly controlled process, which in several cases involves the action of protein cofactors to modulate the activity of the proteinase. Antigens for use in a vaccine can derive from protein precursors.

Figure 2:
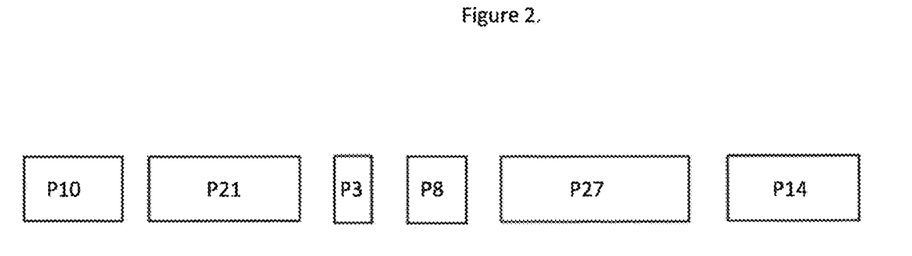
FIG. 2 Illustrates a schematic representation of Pr75gag cleavage products.

In general, MTV proteins are synthesized with at least two major precursor polyproteins for MMTV this includes: gPr75env containing gp52 and gp36; and, Pr75gag containing p27, pp20, p14, and p10. SEQ. 01 illustrates an example sequence for a Pr75gag precursor polyprotein, the cleavage products of which are schematically illustrated in FIG. 2. Shown in FIG. 2, for example, p14 is a signal peptide subunit of an ENV protein. p14 can also function in both oncogenic and an anti-oncogenic capacity depending on its phosphorylation status. Also shown in FIG. 2, p10 is part of the same polyprotein precursor as p14 and is also found as a cleavage product thereof. SEQ. 02 illustrates an example sequence of a p10 protein.

Figure 3:
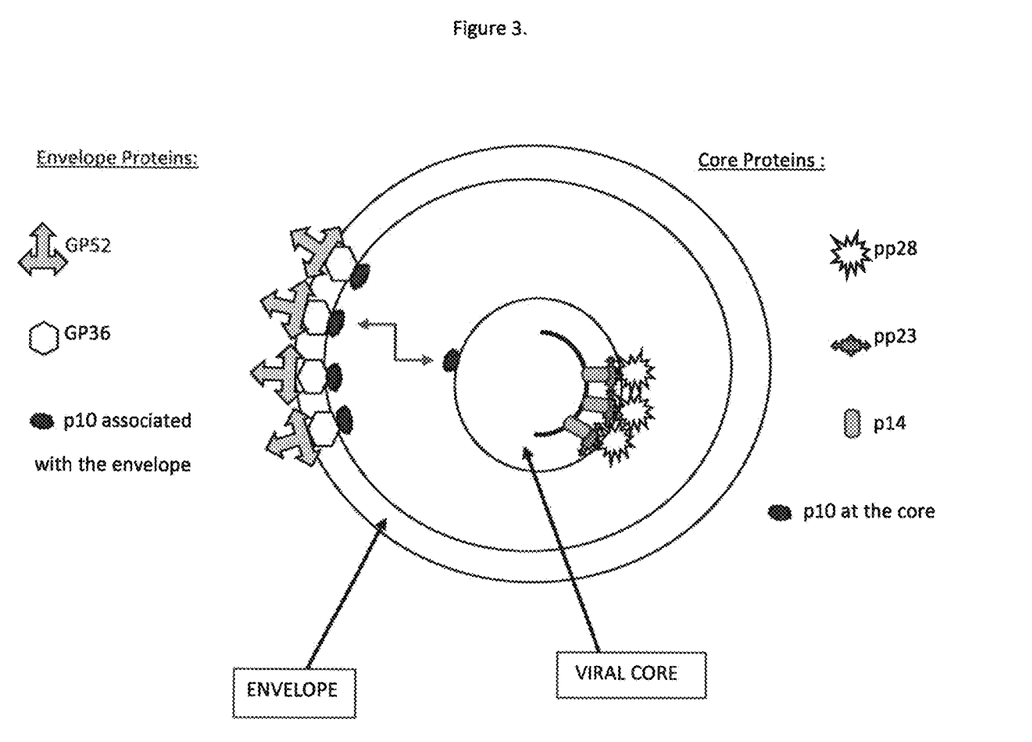
FIG. 3 Illustrates a schematic of an MTV virus.

As illustrated in FIG. 3, p10 initially starts at the viral core and then transitions to the envelope membrane of the virus. This core-to-envelope transition protein is believed to be a representative member of a larger class of core-to-envelope proteins. As used herein the term "transition protein" describes a protein that moves between the viral core and the viral envelope (i.e., from core to envelope or envelope to core). In an embodiment the transition protein may start at the viral core and then move to the viral envelope. The transition protein may thus remain at the underside of the envelope, may transition through the envelope to the exterior, or may span across the viral envelope. A transition protein may also be a protein subunit that forms part of a larger protein. It may be directly produced from viral mRNA or DNA or be the result of cleavage from a precursor polyprotein. Thus, an embodiment of the invention includes an MTV transition protein either alone or in combination with further MTV proteins. The MTV transition protein may also be synthetically generated and combined with other antigens or formed as part of a polyvalent, or compound polyvalent vaccine targeting one or multiple diseases.

Thus, in another embodiment an MTV vaccine preparation containing one or more precursor proteins either derived from polyprotein cleavage products or directly created using alternative protein expression means. In particular polyprotein cleavage products, p11, p14, and, alone or in combination with each other, may be combined with at least one ENV, GAG, or POL protein or protein derivative. Still other embodiments may include GP52, GP36, and P28 proteins. These may then be combined with an MTV transition protein, such as p10.

In addition to MTV, other virus species, termed oncoviruses, are possible sources of oncogenesis; these can include at least: Epstein-Barr Virus (EBV) (Ballard, 2015; Lebreque, 1995), human immunodeficiency virus (HIV), human papilloma virus (HPV), herpes simplex virus (HSV), and bovine leukemia virus (BLV) (Baltzell, 2018; Buehring, 2017). It is believed, without subscribing or limiting to a particular theory, and as briefly outlined above, that viruses often work together to potentiate each other and to cause disease in general. Oncogenic viruses in particular can work together to cause disease. Specifically, RNA viruses tend to be unstable but highly virulent, DNA viruses tend to be stable but not as aggressive. DNA and RNA viruses can work together, each building upon the strengths of the other to increase pathogenicity. It is believed that many viruses like HPV and HSV can make other viruses more virulent, and that certain combinations are particularly effective.

Further, RNA viruses and DNA viruses may have a complimentary effect wherein the high replication and mutation rates of RNA viruses may be stabilized by the less mutagenic DNA viruses, allowing for optimal adaptability without loss of control. The highly active MTV RNA virus replicates quickly and randomly inserts into the genome, often producing no effect. Integrated particles can be found with little to no clinical relevance, and these are often misinterpreted as being endogenous. Once stabilized and directed by a DNA partner, the usually erratic agent can now target its source more effectively and remain consistent long enough to provoke oncogenesis. This is one possible mechanism for HPV/MTV synergy in cancer formation.

Accordingly, embodiments of the invention are directed towards the treatment of breast, prostate, and other viral-mediated cancers or other synergistic diseases in humans and other animals. In some embodiments a protective immunity is formed as a result of vaccination with MTV or synMTV either in whole, in part, or in combinations as part of live, attenuated, or subunit vaccines along with antigenic components of other oncogenic virus particles such as at least: EBV, HIV, HPV, HSV, and BLV. In other embodiments, an MTV vaccine is administered to a patient diagnosed with a viral-mediated cancer with the effect of reducing the malignancy, spread, or recurrence of the viral-mediated cancer.

As noted above, the incidence of breast cancer in humans is increased in areas with increased mouse populations. Also, as above, humans with pets may also experience an increased incidence of breast cancer. Any of the above described vaccines may be altered to target a particular species. For example, a monovalent vaccine targeting a rabbit may use an MTV protein or protein particles purified from rabbit-specific MTV. Likewise, a human targeting vaccine may use ENV protein purified from HMTV strains found in humans. Or, in the alternative, a synthetically derived synProteins or hybrids may be created based upon a target species MTV genetic sequence. In alternative embodiments MTV derived POL or GAG proteins or protein subunits may be used. In an alternative embodiment the vaccine may be composed of particles derived from one or more conserved sequences found across target species, for example, human, mouse, canine, feline, bovine, and other human-companion animals. Thus, an MTV vaccine may be created targeting human associated animals. Additionally, animal vaccination may be used in tandem with human vaccination to decrease the overall incidence of breast cancer in humans by decreasing human exposure to MTV transmitted via animals.

Another embodiment of the invention is a polyvalent vaccine comprised of multiple MTV antigen components. In certain embodiments the components may be a mixture of natural and synthetically derived components, for example, a synthetic synENV mixed with a naturally occurring ENV or POL. The polyvalent vaccine may further contain precursor cleavage products such as p10, p11, or p14. These may further be combined with one or more transition proteins and may be further combined into a combination vaccine.

An embodiment of the invention is a vaccine comprising an MTV transition protein. In some embodiments the MTV transition protein is p10. In some embodiments the vaccine further comprises additional antigens to form a combination vaccine. In still other embodiments the vaccine contains at least one additional MTV component. In some embodiments the one additional MTV component is derived from at least one of: gp52, p14, syngp52, MTV polymerase, synMTV polymerase, MTV transcriptase, synMTV transcriptase, MTV surface, synMTV surface, MTV transmembrane anchoring, synMTV transmembrane anchoring, MTV polysaccharide, and synMTV polysaccharide. In another embodiment there is at least a second MTV component derived from a target species different from the first MTV component. In still other embodiments the vaccine may further contain MTV derived ENV and POL. In still other embodiments at least one of the ENV, POL and MTV transition proteins is synthetically derived. In another embodiment the vaccine may also contain an MTV polysaccharide. In still other embodiments the vaccine may comprise additional antigens to form a combination polyvalent vaccine. In certain embodiments the additional antigens are derived from at least one of: an oncovirus, and a tumor-associated antigen.

In some embodiments the vaccine contains MTV polypeptides coupled to a carrier protein. In certain embodiments the MTV polyeptides are EP3, p14, and an MTV transition protein; and, the carrier protein is KLH. In further embodiments the MTV transition protein is p10. In certain other embodiments the carrier protein is at least one of KLH, Concholepas concholepas hemocyanin, BSA, Cationized BSA, and Ovalbumin. In certain other embodiments the vaccine also contains additional antigens to form a compound polyvalent vaccine.

Another embodiment of the invention is a method of treating MTV where an MTV vaccine with an MTV transition protein is provided and administered. In some embodiments the vaccine is administered in conjunction with additional vaccines. In still other embodiments the vaccine is administered to at least one of a human, and a human associated animal.

Finally, the written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A composition, comprising:
   a protein in the form of protein p10 of SEQ. ID NO: 2; and,
   at least one adjuvant selected from the group of: alum, Complete Freund's Adjuvant, aluminum salt, and calcium salt.

2. The composition of claim 1 further comprising at least one MTV polypeptide selected from the group of: EP3, p14, and an MTV transition protein; and, wherein the p10 of SEQ. ID No: 2 and the at least one MTV polypeptide is coupled to a carrier protein.

3. The composition of claim 2 wherein the carrier protein is at least one selected from the group of:
   KLH, Concholepas concholepas hemocyanin, BSA, Cationized BSA, and Ovalbumin.

4. The composition of claim 1 further comprising: additional antigens.

5. The composition of claim 4 wherein the additional antigens are sourced from at least one selected from the group of: Epstein-Barr Virus (EBV), human immunodeficiency virus (HIV), human papilloma virus (HPV), herpes simplex virus (HSV), and bovine leukemia virus (BLV).

6. The composition of claim 4 wherein the additional antigens are sourced from an RNA virus.

7. The composition of claim 2, further comprising: at least one MTV polypeptide antigen sourced from at least one selected from the group of: gp52, p14, syngp52, MTV polymerase, synMTV polymerase, MTV transcriptase, synMTV transcriptase, MTV surface, synMTV surface, MTV transmembrane anchoring; and, synMTV transmembrane anchoring.

8. The composition of claim 2 further comprising: MTV sourced ENV, and POL.

9. The composition of claim 8 wherein at least one of the ENV, POL, and MTV transition proteins is synthetic.

10. The composition of claim 2 further comprising a polysaccharide.

11. The composition of claim 4 wherein the additional antigens are sourced from an oncovirus.

12. A method, comprising:
    administering to a subject the composition of claim 1.

13. The method of claim 12 further comprising:
    administering the composition of claim 12, in combination with at least one additional medication.

14. The method of claim 12 wherein the subject is a human associated animal.

15. A method comprising the steps of:
    testing for the presence of MTV infection in a subject; and
    administering to the subject a composition comprising p10 of SEQ. ID NO: 2, and at least one adjuvant selected from the group of: alum, Complete Freund's Adjuvant, aluminum salt, and calcium salt.

* * * * *